United States Patent

Pastor et al.

[11] Patent Number: 4,758,614
[45] Date of Patent: Jul. 19, 1988

[54] COMPOSITIONS STABILIZED WITH SUBSTITUTED AMINO CARBAMATES

[75] Inventors: Stephen D. Pastor, Yonkers, N.Y.; Edward T. Hessell, Norwalk, Conn.; Ramanathan Ravichandran, Yonkers, N.Y.

[73] Assignee: Ciba-Geigy Corporation, Ardsley, N.Y.

[21] Appl. No.: 855,662

[22] Filed: Apr. 25, 1986

[51] Int. Cl.$^4$ ............ C08K 5/34; C08K 5/52; C08K 5/09/5/13

[52] U.S. Cl. ............ 524/101; 524/125; 524/141; 524/190; 524/222; 524/240; 524/285; 524/287; 524/289; 524/342; 524/343; 524/350; 252/400.2; 252/400.23; 252/402; 252/403; 252/404

[58] Field of Search ............ 252/402, 403, 404; 524/101, 198, 199, 200, 201, 125, 141, 190, 222, 240, 285, 287, 289, 342, 343, 350; 255/400.2, 400.23

[56] References Cited

U.S. PATENT DOCUMENTS 3,869,278  3/1975  Wilcox ............ 71/121
3,954,770  5/1976  Moyerhoefer et al. ............ 524/200
4,123,413  10/1978  Mark et al. ............ 524/198

FOREIGN PATENT DOCUMENTS 3030014  2/1982  Fed. Rep. of Germany ...... 524/198
2065149  6/1981  United Kingdom .

OTHER PUBLICATIONS

Zinner et al., Pharmazie, 20, 291 (1965).
Konstantinovia, Zhurnol Organ. Khimii, 4, 1928–1932 (1968).
Kliegel, Liebiss Amn. Chem. 736, 173–175 (1970).
Larsen, Aeta Chemical Scandinavia, 27, 843–853 (1968).
Aurich, Chem. Ber. 106, 1881–1895 (1973).

Primary Examiner—John Kight
Assistant Examiner—Kriellion Morgan
Attorney, Agent, or Firm—Harry Falber

[57] ABSTRACT

Substituted amino carbamate derivatives corresponding to the formula

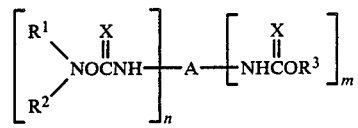

are effective in stabilizing organic materials against oxidative, thermal and actinic degradation, said derivatives being particularly effective as color improvers and process stabilizers in organic materials containing phenolic antioxidants and/or metal salts of fatty acids and/or hindered amine light stabilizers and/or organic phosphorus compounds; and certain of said derivatives as new compounds.

17 Claims, No Drawings

COMPOSITIONS STABILIZED WITH SUBSTITUTED AMINO CARBAMATES

Organic polymeric materials such as plastics and resins are subject to thermal, oxidative and photodegradation. A great variety of stabilizers are known in the art for stabilizing a diversity of substrates. Their effectiveness varies depending upon the causes of degradation and the substrate stabilized. In general, it is difficult to predict which stabilizer will be most effective and most economical for any one area of application. For example, stabilizer effectiveness in reducing volatility may depend upon preventing bond scission in the substrate molecule. Limiting embrittlement and retaining elasticity in a polymer or rubber may require prevention of excessive crosslinking and/or chain scission. Prevention of discoloration may require inhibiting reactions which yield new chromophores or color bodies in the substrate or stabilizer. Problems of process stability and incompatibility must also be considered.

Various organic hydroxylamine compounds are generally known and some are commercially available. A number of patents disclose nitrogen-substituted hydroxylamines as antioxidant stabilizers for various substrates including polyolefins, polyesters and polyurethanes. U.S. Pat. Nos. 3,432,578, 3,644,278, 3,778,464, 3,408,422, 3,926,909, 4,316,996 and 4,386,224 are representative of such patents which basically disclose N,N-dialkyl-, N,N-diaryl- and N,N-diaralkyl hydroxylamine compounds and their color improvement and color stabilizing activity.

In addition, several carbamoyl-substituted hydroxylamine compounds are disclosed in U.S. Pat. No. 3,869,278 and Zinner et al, Pharmazie, 20, 291 (1965) in a non-polymeric context. The reaction of N,N-dimethyl, N,N-diethyl, and N,N-diisopropyl-hydroxylamine with isocyanates to prepare N,N-dialkyl-O-carbamoylhydroxylamines along with the potential herbicidal activity of such compounds has been described by N. V. Konstantinovia et al., Zhurnol Organicheskoi Khimii, 4, 1928–1932 (1968). The reaction of benzhydryl-substituted hydroxylamines has been described by von Wolfgang Kliegel et al., Liebigs Ann. Chem., 736, 173–175 (1970). O-Carbamoylhydroxylamine has been described by I. K. Larsen, Acta Chemical Scandinovia, 22, 843–853 (1968). The reaction of N-acyl-N-alkylhydroxylamines with isocyanates is mentioned by H. G. Aurich et al., Chem. Ber., 106, 1881–1896 (1973). The latter technical publications are devoid of utility statements for the compounds.

It has now been determined that the compositions of this invention exhibit a variety of desirable properties stemming from the presence therein of the indicated substituted amino carbamates. Thus, the compounds serve to protect various substrates such as polyolefins, elastomers and lubricating oils against the adverse effects of oxidative and thermal degradation. They are most effective as color improvers and process stabilizers in polyolefin compositions which may contain metal salts of fatty acids and which also contain a phenolic antioxidant. Thus, they serve to substantially reduce color formation resulting from the presence of the phenolic antioxidant and/or from the processing conditions as well as to directly protect the polymer from said processing conditions. They also prevent the discoloration of polyolefin compositions containing hindered amine light stabilizers or combinations of phenolic antioxidants and organic phosphites. In addition, the gas fading that may be experienced upon exposure to the combustion products of natural gas is also significantly reduced.

It is a primary object of this invention to provide compositions of organic materials stabilized against oxidative, thermal and actinic degradation by the presence therein of a class of substituted aminoxy carbamate derivatives.

It is a further object to provide such compositions which also contain phenolic antioxidants wherein said carbamates substantially reduce color formation resulting from the presence of said phenol.

It is still a further object to provide a class of novel carbamate derivatives which exhibits a broad range of improved stabilization performance characteristics.

Various other objects and advantages of this invention will become evident from the following description thereof.

The stabilizing compounds utilized in the compositions of this invention correspond to the formula

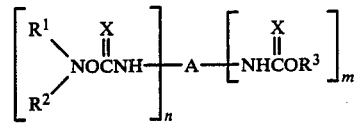

wherein n is 1 to 3;

m is 0 to 2;

n+m is 1 to 3;

$R^1$ and $R^2$ are independently hydrogen, alkyl of 1 to 36 carbon atoms, said alkyl substituted by halogen, alkoxyalkyl of 2 to 6 carbon atoms, cycloalkyl of 5 to 12 carbon atoms, aralkyl of 7 to 9 carbon atoms or said aralkyl substituted by alkyl of 1 to 36 carbon atoms, $R^3$ is alkyl of 1 to 18 carbon atoms;

X is oxygen or sulfur;

A, when n=1 and m=0, is hydrogen, alkyl of 1 to 36 carbon atoms, said alkyl substituted by halogen, alkoxyalkyl of 2 to 6 carbon atoms, cycloalkyl of 5 to 12 carbon atoms, aryl, aralkyl of 7 to 9 carbon atoms, said aralkyl substituted by alkyl of 1 to 36 carbon atoms or aryloxyalkyl($C_2$-$C_6$);

A, when n+m=2, is alkylene of 1 to 12 carbon atoms, alkylidene of 2 to 12 carbon atoms, cycloalkylene of 6 to 10 carbon atoms, ($C_1$-$C_4$)alkyl-substituted hexahydrobenzylene, arylene of 6 to 10 carbon atoms, or 4,4'-alkylidenediphenyl; and A, when n+m=3, is alkanetriyl of 3 to 12 carbon atoms or tris($C_2$-$C_6$ alkylene)isocyanurate.

The $R^1$ and $R^2$ groups are preferably hydrogen, straight-chain or branched alkyl with 1 to 18 carbon atoms such as methyl, ethyl, n-propyl, n-butyl, tert-butyl, n-pentyl, n-octyl, 2-ethylhexyl, decyl, dodecyl and octadecyl; cyclopentyl and cyclohexyl; and benzyl, α-methylbenzyl and α,α-dimethylbenzyl. X is preferably oxygen. $R^3$ is preferably $C_{12}$-$C_{18}$ alkyl.

Other preferred groups include, for n=1 and m=0, A as $C_1$-$C_{18}$ alkyl (see preferred list for $R^1$ and $R^2$) and phenyl; for n+m=2, A as alkylene of 2 to 6 carbon atoms, e.g. ethylene, propylene or hexylene, alkylidene of 1 to 6 carbon atoms such as ethylidine, cyclohexylene, trimethyl-hexahydrobenzylene, phenylene, xylylene, 2,4-tolylene and 4,4-methylenediphenyl; and for n+m=3, A as glyceryl and trimethylylpropane.

The derivatives of this invention can be prepared by reacting the appropriately substituted hydroxylamine with an appropriately substituted isocyanate, isothiocyanate or cyanate salt (A=H) in a solvent to yield the desired product. Typical isocyanate reactants include n-butyl isocyanate, n-hexyl isocyanate, n-octadecyl isocyanate, phenyl isocyanate, 2,4-toluenediisocyanate, potassium cyanate, 1,6-hexanediisocyanate, ethyl isothiocyanate, phenyl isothiocyanate and naphthyl isothiocyanate. The solvent can be an aromatic hydrocarbon such as benzene, toluene, xylene, and the like, or a heterocyclic ether, such as tetrahydrofuran. The reaction temperature ranges from 10° to 70° C. Where di- and tris-carbamates with m=1 or 2 are prepared, the remaining O-substituents are provided by reacting the hydroxylamine/isocyanate reaction product with the appropriate alcohol ($R^3OH$) at a temperature of 20° to 70° C. The starting materials needed to prepare the stabilizers of this invention are items of commerce or can be prepared by known methods.

The compounds of the present invention are particularly effective in stabilizing organic materials subject to oxidative, thermal and actinic degradation, such as plastics, polymers and resins.

Substrates in which these compounds are particularly useful are polyolefins such as polyethylene and polypropylene; polystyrene, including impact polystyrene, ABS resin, SBR, isoprene, as well as natural rubber, polyesters including polyethylene terephthalate and polybutylene terephthalate, including copolymers, and lubricating oils such as those derived from mineral oil.

In general polymers which can be stabilized include

1. Polymers of monoolefins and diolefins, for example polyethylene (which optionally can be crosslinked), polyproplene, polyisobutylene, polybutene-1, polymethylpentene-1, polyisoprene or polybutadiene, as well as polymers of cycloolefins, for instance of cyclopentene or norbornene.

2. Mixtures of the polymers mentioned under (1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under (5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrine homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under (8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamid or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane]terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methylcellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene/butadiene coploymers.

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain various conventional additives, such as the following.

1. Antioxidants 1.1. Alkylated monophenols, for example,
2,6-di-tert.butyl-4-methylphenol
2-tert.butyl-4,6-dimethylphenol
2,6-di-tert.butyl-4-ethylphenol
2,6-di-tert.butyl-4-n-butylphenol
2,6-di-tert.butyl-4-i-butylphenol
2,6-di-cyclopentyl-4-methylphenol
2-($\alpha$-methylcyclohexyl)-4,6-dimethylphenol
2,6-di-octadecyl-4-methylphenol
2,4,6-tri-cyclohexylphenol
2,6-di-tert.butyl-4-methoxymethylphenol 1.2. Alkylated hydroquinones, for example,
2,6-di-tert.butyl-4-methoxyphenol
2,5-di-tert.butyl-hydroquinone
2,5-di-tert.amyl-hydroquinone
2,6-diphenyl-4-octadecyloxyphenol 1.3. Hydroxylated thiodiphenyl ethers, for example
2,2'-thio-bis-(6-tert.butyl-4-methylphenol)
2,2'-thio-bis-(4-octylphenol)
4,4'-thio-bis-(6-tert.butyl-3-methylphenol)
4,4'-thio-bis-(6-tert.butyl-2-methylphenol)

1.4. Alkyliden-bisphenols, for example,
2,2'-methylene-bis-(6-tert.butyl-4-methylphenol)
2,2'-methylene-bis-(6-tert.butyl-4-ethylphenol)
2,2'-methylene-bis-[4-methyl-6-($\alpha$-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-($\alpha$-methylbenzyl)-4-nonylphenol]
2,2'-methylene-bis-[6-($\alpha,\alpha$-dimethylbenzyl)-4-nonylphenol]
2,2'-methylenen-bis-(4,6-di-tert.butylphenol)
2,2'-ethylidene-bis-(4,6-di-tert.butylphenol)
2,2'-ethylidene-bis-(6-tert.butyl-4-isobutylphenol)
4,4'-methylene-bis-(2,6-di-tert.butylphenol)
4,4'-methylene-bis-(6-tert.butyl-2-methylphenol)
1,1-bis-(5-tert.butyl-4-hydroxy-2-methylphenyl-butane
2,6-di-(3-tert.butyl-5-methyl-2-hydroxybenzyl)-4-methylphenol
1,1,3-tris-(5-tert.butyl-4-hydroxy-2-methylphenyl)-butane
1,1-bis-(5-tert.butyl-4-hydroxy-2-methylphenyl)-3-n-dodecylmercaptobutane
ethyleneglycol-bis-[3,3-bis-(3'-tert.butyl-4'-hydroxyphenyl)-butyrate]
di-(3-tert.butyl-4-hydroxy-5-methylphenyl)-dicyclopentadiene
di-[2-(3'-tert.butyl-2'-hydroxy-5'-methyl-benzyl)-6-tert.-butyl-4-methylphenyl]-terephthalate.

1.5. Benzyl compounds, for example,
1,3,5-tri-(3,5-di-tert.butyl-4-hydroxybenzyl)-2,4,6-trimethylbenzene-di-(3,5-di-tert.butyl-4-hydroxybenzyl)-sulfide
3,5-di-tert.butyl-4-hydroxybenzyl-mercapto-acetic acid isooctyl ester
bis-(4-tert.butyl-3-hydroxy-2,6-dimethylbenzyl)dithiol-terephthalate
1,3,5-tris-(3,5-di-tert.butyl-4-hydroxybenzyl)-isocyanurate
1,3,5-tris-(4-tert.butyl-3-hydroxy-2,6-dimethylbenzyl)-isocyanurate
3,5-di-tert.butyl-4-hydroxybenzyl-phosphoric acid-dioctadecyl ester
3,5-di-tert.butyl-4-hydroxybenzyl-phosphoric acid-monoethyl ester, calcium-salt 1.6. Acylaminophenols, for example,
4-hydroxy-lauric acid anilide
4-hydroxy-stearic acid anilide
2,4-bis-octylmercapto-6-(3,5-tert.butyl-4-hydroxyanilino)-s-triazine
octyl-N-(3,5-di-tert.butyl-4-hydroxyphenyl)-carbamate 1.7. Esters of $\beta$-(3,5-di-tert.butyl-4-hydroxyphenyl)-propionic acid with monohydric or polyhydric alcohols, for example,

| | |
|---|---|
| methanol | diethyleneglycol |
| octadecanol | triethyleneglycol |
| 1,6-hexanediol | pentaerythritol |
| neopentylglycol | tris-hydroxyethly isocyanurate |
| thiodiethyleneglycol | di-hydroxyethyl oxalic acid diamide |

1.8. Esters of β-(5-tert.butyl-4-hydroxy-3-methylphenyl)-opionic acid with monohydric or polyhydric alcohols, for example,

| | |
|---|---|
| methanol | diethyleneglycol |
| octadecanol | triethyleneglycol |
| 1,6-hexanediol | pentaerythritol |
| neopentylglycol | tris-hydroxyethly isocyanurate |
| thiodiethyleneglycol | di-hydroxyethyl oxalic acid diamide |

1.9. Amides of β-(3,5-di-tert.butyl-4-hydroxyphenyl)-propionic acid for example,
N,N'-di-(3,5-di-tert.butyl-4-hydroxyphenylpropionyl)-hexamethylendiamine
N,N'-di-(3,5-di-tert.butyl-4-hydroxyphenylpropionyl)-trimethylendiamine
N,N'-di-(3,5-di-tert.butyl-4-hydroxyphenylpropionyl)-hydrazine 2. UV absorbers and light stabilisers 2.1. 2-(2'-Hydroxyphenyl)-benztriazoles, for example, the 5'-methyl-, 3',5'-di-tert.butyl-, 5'-tert.butyl-, 5'-(1,1,3,3-tetramethylbutyl)-, 5-chloro-3',5'-di-tert.-butyl-, 5-chloro-3'-tert.butyl-5'-methyl-, 3'-sec.butyl-5'-tert.butyl-, 4'-octoxy, 3',5'-di-tert.amyl-, 3',5'-bis-(α,α-dimethylbenzyl)-derivative.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivative.

2.3. Esters of optionally substituted benzoic acids for example, phenyl salicylate, 4-tert.butyl-phenylsalicylate, octylphenyl salicylate, dibenzoylresorcinol, bis-(4-tert.-butylbenzoyl)-resorcinol, benzoylresorcinol, 3,5-di-tert.-butyl-4-hydroxybenzoic acid 2,4-di-tert.butylphenyl ester and 3,5-di-tert.-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-di-ethanolamine, nickel dibutyldithiocarbamate, nickel salts of 4-hydroxy-3,5-di-tert.butylbenzylphosphonic acid monoalkyl ester, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazol, optionally with additional ligands.

2.6. Sterically hindered amines, for example bis-(2,2,6,6-tetramethylpiperidyl)-sebacate, bis-(1,2,2,6,6-pentamethylpiperidyl)-sebacate, n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylendiamine and 4-tert.octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butanetetracarbonic acid, 1,1'(1,2-ethanediyl)-bis-(3,3,5,5-tetramethylpiperazinone).

2.7. Oxalic acid diamides, for example, 4,4'-di-octyloxyoxanilide, 2,2'-di-octyloxy-5,5'-di-tert.butyloxanilide, 2,2'-di-dodecyloxy-5,5'-di-tert.butyl-oxanilide, 2-ethoxy-2'-ethyl-oxanilide, N,N'-bis(3-dimethylaminopropyl)-oxalamide, 2-ethoxy-5-tert.butyl-2'-ethyloxanilide and its mixture with 2-ethoxy-2'-ethyl-5,4'-di-tert.butyloxanilide and mixtures of ortho- and para-methoxy-as well as of o- and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert.butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl)phosphite, trilauryl phosphite, trioctadecyl phosphite, di-stearyl-pentaerythritol diphosphite, tris-(2,4-di-tert.butylphenyl)-phosphite, di-isodecylpentaerythritol diphosphite, di-(2,4-di-tert.-butylphenyl)pentaerythritol diphosphite, tristearyl-sorbitol triphosphite, tetrakis-(2,4-di-tert.butylphenyl)-4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc-dibutyl-dithiocarbamate, dioctadecyldisulfide, pentaerythritol-tetrakis-(β-dodecylmercapto)-propionate.

6. Polyamide stabilisers, for example copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for example, 4-tert.butyl-benzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxides, carbon black, graphite.

10. Other additives, for example, plasticizers, lubricants, emulsifiers, pigments, optical brighteners, flameproofing agents, anti-static agents, blowing agents and thiosynergists such as dilaurylthiodipropionate or distearylthiodipropionate.

While the instant amino carbamates can be beneficially used as stablizers for a variety of substrates, particularly the polyolefins, both alone and in conjunction with other coadditives, the introduction of the instant amino carbamates into polyolefins, optionally containing various alkali metal, alkaline earth metal and aluminum salts of higher fatty acids (see Additive #7 hereinabove), with hindered phenolic antioxidants exhibits enhanced and particularly salubrious protection to such substrates in terms of reducing color formation stemming from the presence of the phenols. Such phenolic antioxidants include n-cotadecyl 3,5-di-tert-butyl-4-hydroxyhydrocinnamate, neopentanetetrayl tetrakis-(3,5-di-tert-butyl-4-hydroxyl-hydrocinnamate), di-n-octadecyl 3,5-di-tert-butyl-4-hydroxybenzylphosphonate, 1,3,5-tris(3,5-di-tert-butyl-4-hydroxybenzyl-)isocyanurate, thiodiethylene bis(3,5-di-tert-butyl-4-hydroxyhydrocinnamate), 1,3,5-trimethyl-2,4,6-tris (3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris-(2,6-di-methyl-4-tert-butyl-3-hydroxybenzyl)isocyanurate, 1,1,3-tris-(2-methyl-4-hydroxy-5-tert-butylphenyl)butane, 1,3,5-tris-[2-(3,5-di-tert-butyl-4-hydroxyhydrocinnamoyloxy)-ethyl]-isocyanurate, 3,5-di-(3,5-di-tert-butyl-4-hydroxybenzyl)-mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl-3,5-di-tert-butyl-4-hydroxybenzylphosphonate), ethylene bis[3,3-di-(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis-[2-(3,5-tert-butyl-4-hydroxyhydroxo-cinnamoyloxy)ethyl]-oxamide, and preferably neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris-( 3,5-di-tert-butyl-4-hydroxybenzyl)isocyanurate, 2,6-di-tert-butyl-p-cresol or 2,2'-ethylidene-bis(4,6-di-tert-butylphenol).

Likewise, the instant compounds prevent color formation when hindered amine light stabilizers are present, such hindered amines including bis(1,2,2,6,6-pentamethyl-4-piperidyl)-2-n-butyl-2-(3,5-di-tert-butyl-4-hydroxybenzyl)malonate; bis(2,2,6,6-tetramethyl-4-piperidyl)sebacate; dimethylsuccinate polymer with 4-hydroxy-2,2,6,6-tetramethyl-1-piperidinethanol; and polymer of 2,4-dichloro-6-octylamino-s-triazine with N'-(2,2,6,6-tetramethyl-4-piperidyl)hexamethylene diamine.

As previously noted, certain amino carbamate derivatives also form part of the instant invention. These derivatives correspond to the above noted generic formula wherein all the defined substituents are identical except for the n+m value which is 2 or 3. The preferred substituents, preparative procedures and utility statements noted hereinabove equally apply to these novel carbamate derivatives.

The following examples illustrate the embodiments of this invention. Thus, they describe the preparation of various carbamates, including those forming part of the invention, and of stabilized compositions. In these examples, all parts given are by weight unless otherwise specified.

EXAMPLE 1

N-Butyl-O-(N,N-dibenzylamino)carbamate

A solution of 5.33 g (25 mmol) of N,N-dibenzylhydroxylamine in 25 ml of dry tetrahydrofuran is admixed with 2.48 g (25 mmol) of n-butyl isocyanate and the mixture is stirred for four hours. The solvent is removed in vacuo and the residue is recrystallized from heptane to give 6.8 g (87%) of a white solid, m.p. 81°–82° C.

Anal. Calcd. for $C_{19}H_{24}N_2O_2$: C, 73.0; H, 7.7; N, 9.0. Found: C, 73.0; H, 7.7; N, 8.8.

EXAMPLE 2

N-Phenyl-O-(N,N-dibenzylamino)carbamate

The procedure of Example 1 is repeated using 5.33 g (25 mmol) N,N-dibenzylhydroxylamine and 2.98 g (25 mmol) of phenyl isocyanate. The residue is recrystallized from a heptane-toluene solvent mixture to give 5.8 g (70%) of a white solid, m.p. 120°–123° C.

Anal. Calcd. for $C_{21}H_{20}N_2O_2$: C, 75.9; H, 6.1; N, 8.4. Found: C, 75.6; H, 5.9; N, 8.3.

EXAMPLE 3

N-n-Octadecyl-O-(N,N-dibenzylamino)carbamate

The procedure of Example 1 is repeated using 5.33 g (25 mmol) of N,N-dibenzylhydroxylamine and 7.38 g (12.5 mmol) of n-octadecyl isocyanate. The residue is recrystallized from heptane to give 9.0 g (71%) of a white solid, m.p. 63°–66° C.

EXAMPLE 4

N,N'-(1,6-Hexanediyl)-bis[O-(N,N-dibenzylamino)carbamate]

The procedure of Example 1 is repeated using 5.33 g (25 mmol) of N,N-dibenzylhydroxylamine and 2.10 g (1.25 mmol) of 1,6-hexanediisocyanate. The residue is recrystallized from 2-propanol to give 6.6 g (89%) of a white solid, m.p. 121°–124' C.

Anal. Calcd. for $C_{36}H_{42}N_4O_4$: C, 72.7; H, 7.1; N, 9.3. Found: C, 72.6; H, 7.1; N, 9.4.

EXAMPLE 5

N,N'-(4-Methyl-1,3-phenylene)-di[O-(N,N-dibenzylamino)carbamate]

The procedure of Example 1 is repeated using 42.66 g (0.2 mole) of N,N-dibenzylhydroxylamine and 17.42 g (0.1 mole) of 2,4-toluene diisocyanate to give 57.0 g of a white solid; m.p. 48°–55° C.

Anal. Calcd. for $C_{37}H_{36}N_4O_4$: C, 74.0; H, 6.0; N, 9.3. Found: C, 73.6; H, 6.1; N, 9.1.

EXAMPLE 6

N,N'-(4-Methyl-1,3-phenylene)-O-(N,N-dibenzylamino)-O-(n-octadecyl)dicarbamate

A stirred mixture of 21.33 g (0.1 mole) of N,N-dibenzylhydroxylamine in 100 ml tetrahydrofuran is admixed dropwise with 17.42 g (0.1 mole) of 2,4-toluene diisocyanate. The reaction mixture is stirred at room temperature until the reaction is complete as determined by the disappearance of the hydroxyl absorption in the IR spectrum of the reaction mixture. To the resultant reaction mixture is added 27.05 g (0.1 mole) of n-octadecyl alcohol. The reaction mixture is heated at reflux for 14 hours. Upon cooling, the resultant solid is removed by filtration and the solid is recrystallized twice from acetone to give 12.31 g of a white solid; mp 90°–97° C.

EXAMPLE 7

N,N-Dibenzyl-O-carbamylhydroxylamine

A stirred suspension of 10.70 g of N,N-dibenzylhydroxylamine in 25 ml of methanol is admixed dropwise with a solution of 4.53 ml conc. hydrochloric acid in 10 ml of water. A solution of 4.06 g of potassium cyanate in 15 ml of water is then added and the resulting suspension is stirred at room temperature for 3 hours. The crude product is removed by filtration and further purified by liquid chromatography to afford the title compound as a white solid; m.p. 127°–29° C.

Anal. Calcd. for $C_{15}H_{16}N_2O_2$: C, 70.3; H, 6.3; N, 10.9. Found: C, 70.2; H, 6.3; N, 11.2.

EXAMPLE 8

N-n-Hexyl-O-(N,N-dibenzylamino)carbamate

The procedure of Example 1 is repeated using 5.33 g (25 mmol) of N,N-dibenzylhydroxylamine and 3.18 g (25 mmol) of n-hexyl isocyanate. The residue is recrystallized from heptane to give 7.5 g (88%) of a white solid, m.p. 72°–73.5° C.

Anal. Calcd. for $C_{21}H_{28}N_2O_2$: C, 74.1; H, 8.3; N, 8.2. Found: C, 74.4; H, 8.2; N, 8.2.

EXAMPLE 9

1-{N-[O-(N,N-dibenzylamino)carboxy]amino}-3-{N-[O-(N,N-dibenzylamino)carboxy]amino}methyl-3,5,5-trimethylcyclohexane.

The procedure of Example 1 is repeated using 10.66 g (50 mmol) of N,N-dibenzylhydroxylamine and 5.56 g (25 mmole) of 3-isocyanatomethyl-3,5,5-trimethylcyclohexylisocyanate. The residue is recrystallized from a 1:1 heptane:toluene solvent mixture to give 11.0 g (68%) of a white soldi, m.p. 139°–146° C.

Anal. Calcd. for $C_{40}H_{48}N_4O_4$: C, 74.0; H, 7.5; N, 8.6. Found: C, 74.0; H, 7.7; N, 8.7.

EXAMPLE 10

Condensation product of N,N-dibenzylhydroxylamine and N,N′,N″-tris(6-isocyanatohexyl)-2,4,6-trioxo-1,3,5-cyclohexatriazine.

The procedure of Example 1 is repeated using 5.33 g (25 mmol) of N,N-dibenzylhydroxylamine and 4.66 g of a 90%, by weight, solution of N,N′N″-tris(6-isocyanatohexyl)-2,4,6-trioxo-1,3,5-cyclohexyltriazine in n-butyl acetate. The residue, 8.7 g (92%), needs no further purification.

Anal. Calcd. for $C_{66}H_{81}N_9O_9$: C, 69.3; H, 7.1. Found: C, 69.4; H, 7.1.

EXAMPLE 11

Processing of Polypropylene

Base Formulation

| | |
|---|---|
| Polypropylene* | 100 parts |
| Calcium Stearate | 0.10 part |

*Profax 6501 from Himont USA

The indicated stabilizers are solvent blended into polypropylene as solutions in methylene chloride and after removal of solvent by evaporation at reduced pressure, the resin is extruded using the following extruder conditions:

| | Temperature (°C.) |
|---|---|
| Cylinder #1 | 232 |
| Cylinder #2 | 246 |
| Cylinder #3 | 260 |
| Gate #1 | 260 |
| Gate #2 | 260 |
| Gate #3 | 260 |
| RPM 100 | |

During extrusion, the internal extruder pressure is determined using a pressure transducer. After each of the first, third and fifth extrusions, resin pellets are compression molded into 125 mil (3.2 mm) thick plaques at 193° C. and specimen yellowness index (Y.I.) determined according to ASTM D1925-63T.

The melt flow rate (MFR) is determined by ASTM method 1238 condition L. The melt flow rate varies inversely as the transducer pressure and both are a measure of the molecular weight for a specific type of polymer. The results are shown in the following table.

| Additives | Extrusion Temperature 260° C. YI Color After Extrusion | | | Melt Flow Rate After Extrusion (g/10 Min) | |
|---|---|---|---|---|---|
| | 1 | 3 | 5 | 1 | 5 |
| Base Resin | 3.6 | 3.9 | 4.6 | 4.4 | 11.5 |
| 0.1% Antioxidant A | 6.1 | 7.9 | 9.4 | 2.5 | 4.2 |
| 0.1% Antioxidant A + 0.05% Ex. 1 | 2.9 | 3.4 | 6.5 | 2.2 | 4.1 |
| 0.1% Antioxidant A + 0.05% Ex. 2 | 3.9 | 5.4 | 7.4 | 1.9 | 3.8 |

Antioxidant A—Neopentyl tetrakis [3-(3′-5′-di-tert-butyl-4′-hydroxyphenyl)propanoate]

These data thus indicate the effective color improving and process stabilization characteristics of the instant compounds.

Summarizing, it is seen that this invention provides organic materials stabilized against degradation by the presence therein of various amino carbamates as well as certain of said amino carbamates. Variations may be made in proportions, procedures and materials without departing from the scope of the invention as defined by the following claims.

What is claimed is:

1. A composition of matter comprising a plastic, polymer, resin and oil subject to oxidative, thermal and actinic degradation stabilized with an effective stabilizing amount of a compound of the formula

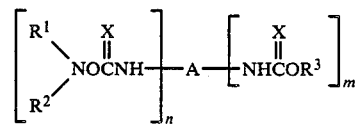

wherein
n is 1 to 3;
m is 0 to 2;
n+m is 1 to 3;
$R^1$ and $R^2$ are independently hydrogen, alkyl of 1 to 36 carbon atoms, said alkyl substituted by halogen, alkoxyalkyl of 2 to 6 carbon atoms, cycloalkyl of 5 to 12 carbon atoms, aralkyl of 7 to 9 carbon atoms or said aralkyl substituted by alkyl of 1 to 36 carbon atoms,
$R^3$ is alkyl of 1 to 18 carbon atoms;
X is oxygen or sulfur;

A, when n=1 and m=0, is hydrogen, alkyl of 1 to 36 carbon atoms, said alkyl substituted by halogen, alkoxyalkyl of 2 to 6 carbon atoms, cycloalkyl of 5 to 12 carbon atoms, aryl, aralkyl of 7 to 9 carbon atoms, said aralkyl substituted by alkyl of 1 to 36 carbon atoms or aryloxyalkyl($C_2$–$C_6$);

A, when n+m=2, is alkylene of 1 to 12 carbon atoms, alkylidene of 2 to 12 carbon atoms, cycloalkylene of 6 to 10 carbon atoms, ($C_1$–$C_4$)alkyl-substituted hexahydrobenzylene, arylene of 6 to 10 carbon atoms, or 4,4'-alkylidenediphenyl; and A, when n+m=3, is alkanetriyl of 3 to 12 carbon atoms or tris($C_2$–$C_6$alkylene)isocyanurate.

2. The composition of claim 1, wherein $R^1$ and $R^2$ are independently hydrogen, straight-chain or branched alkyl of 1 to 18 carbon atoms, cyclopentyl, cyclohexyl, benzyl, α-methylbenzyl or α,α-dimethylbenzyl.

3. The composition of claim 2, wherein $R^1$ and $R^2$ are benzyl.

4. The composition of claim 1, wherein X is oxygen.

5. The composition of claim 1, wherein n is 1, m is 0 and A is $C_1$–$C_{18}$ alkyl or phenyl.

6. The composition of claim 1, wherein n is 1 and m is 1 or n is 2 and m is 0, and A is alkylene of 2 to 6 carbon atoms, alkylidene of 2 to 6 carbon atoms, cyclohexylene, trimethyl-hexahydrobenzylene, phenylene, xylylene, 2,4-tolylene or 4,4'-methylenediphenyl.

7. The composition of claim 1, wherein n is 1 and m is 2, n is 2 and m is 1 or n is 3 and m is 0, and A is glyceryl or trimethylylpropane.

8. The composition of claim 5, wherein said compound is N-butyl-O-(N,N-dibenzylamino)carbamate.

9. The composition of claim 5, wherein said compound is N-phenyl-O-(N,N-dibenzylamino)carbamate.

10. The composition of claim 1, wherein the polymer is a synthetic polymer.

11. The composition of claim 10, wherein the synthetic polymer is a polyolefin homopolymer or copolymer.

12. The composition of claim 11 which also contains a metal salt of a higher fatty acid.

13. The composition of claim 1, which also contains a phenolic antioxidant.

14. The composition of claim 12 which also contains a phenolic antioxidant.

15. The composition of claim 13, wherein said phenolic antioxidant is selected from the group consisting of n-octadecyl 3,5-di-tert-butyl-4-hydroxyhydrocinnamate, neopentanetetrayl tetrakis-(3,5-di-tert-butyl-4-hydroxylhydrocinnamate), di-n-octadecyl 3,5-di-tert-butyl-4-hydroxybenzyl-phosphonate, 1,3,5-tris(3,5-di-tert-butyl-4-hydroxy-benzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-di-oxaocta-methylene bis(3-methyl-5-tert-butyl-4-hydroxyhydro-cinnamate), 2,6-di-tert-butyl-p-cresol, 2,2'-ethylidene-bis(4,6-di-tert-butylphenol), 1,3,5-tris(2,6-di-methyl-4-tert-butyl-3-hydroxybenzyl)isocyanurate, 1,1,3-tris-(2-methyl-4-hydroxy-5-tert-butylphenyl)butane, 1,3,5-tris-[2-(3,5-di-tert-butyl-4-hydroxyhydro-cinnamoyloxy)-ethyl]-isocyanurate, 3,5-di-(3,5-di-tert-butyl-4-hydroxybenzyl)-mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-tert-butyl-4-hydroxyhydroxocinnamoyloxy)ethyl]oxamide.

16. The composition of claim 15, wherein said phenolic antioxidant is selected from the group consisting of neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris-(3,5-di-tert-butyl-4-hydroxybenzyl)isocyanurate, 2,6-di-tert-butyl-p-cresol and 2,2'-ethylidene-bis(4,6-di-tert-butylphenol).

17. A method for stabilizing an plastic, polymer, resin and oil against oxidative, thermal and actinic degradation which comprises incorporating into said plastic, polymer, resin and oil an effective stabilizing amount of a compound of claim 1.

* * * * *